US011967416B2

(12) United States Patent
Etemadi

(10) Patent No.: US 11,967,416 B2
(45) Date of Patent: Apr. 23, 2024

(54) IMAGE ANALYSIS AND INSIGHT GENERATION

(71) Applicant: Northwestern Memorial Healthcare, Chicago, IL (US)

(72) Inventor: Mozziyar Etemadi, Chicago, IL (US)

(73) Assignee: Northwestern Memorial Healthcare, Chicago, IL (US)

( * ) Notice: Subject to any disclaimer, the term of this patent is extended or adjusted under 35 U.S.C. 154(b) by 0 days.

(21) Appl. No.: 18/297,051

(22) Filed: Apr. 7, 2023

(65) Prior Publication Data

US 2023/0274818 A1 Aug. 31, 2023

Related U.S. Application Data

(63) Continuation of application No. PCT/US2023/061179, filed on Jan. 24, 2023.

(60) Provisional application No. 63/393,116, filed on Jul. 28, 2022, provisional application No. 63/302,799, filed on Jan. 25, 2022.

(51) Int. Cl.
*G16H 30/40* (2018.01)
*G06T 7/00* (2017.01)
*G16H 15/00* (2018.01)

(52) U.S. Cl.
CPC .......... *G16H 30/40* (2018.01); *G06T 7/0012* (2013.01); *G16H 15/00* (2018.01); *G06T 2207/20081* (2013.01); *G06T 2207/20084* (2013.01); *G06T 2207/30004* (2013.01)

(58) Field of Classification Search
CPC ...... G16H 15/00; G16H 30/40; G06T 7/0012; G06T 2207/20081; G06T 2207/20084; G06T 2207/30004
See application file for complete search history.

(56) References Cited

U.S. PATENT DOCUMENTS

| 10,452,813 | B2 | 10/2019 | Sorenson et al. |
| 10,977,796 | B2 * | 4/2021 | Vincent ................. G16H 30/20 |
| 11,238,588 | B2 * | 2/2022 | Kawagishi .............. G06N 5/04 |
| 11,244,755 | B1 * | 2/2022 | Syeda-Mahmood .... G06N 3/04 |
| 2016/0350919 | A1 * | 12/2016 | Steigauf ................. G16H 40/20 |

(Continued)

FOREIGN PATENT DOCUMENTS

WO 2017152121 A1 9/2017

OTHER PUBLICATIONS

GE Healthcare "Marquette 12SL Algorithm Connected Clinical Excellence" General Electric Company (2016), 10 pgs.

(Continued)

*Primary Examiner* — Nay A Maung
*Assistant Examiner* — Jose M Torres
(74) *Attorney, Agent, or Firm* — Hogan Lovells US LLP

(57) ABSTRACT

Approaches for analyzing an input image and providing one or more outputs related to the input image are provided. In accordance with an exemplary embodiment, an input image may be received and analyzed, using a trained machine learning model, to generate an inference related to the image. Based, at least in part, upon the generated inference, one or more reports related to the inference can be generated and provided for presentation on a user device. A user can interact with the report in a conversational manner with the computer system to generate additional reports or insights related to the input image.

15 Claims, 8 Drawing Sheets

(56) References Cited

U.S. PATENT DOCUMENTS

| | | | |
|---|---|---|---|
| 2018/0055468 A1* | 3/2018 | Reicher | A61B 5/743 |
| 2019/0088359 A1* | 3/2019 | Moore | G06F 16/5838 |
| 2020/0211692 A1* | 7/2020 | Kalafut | G06N 20/00 |
| 2020/0250336 A1* | 8/2020 | Stockert | G16H 40/40 |
| 2020/0321101 A1 | 10/2020 | Karargyris et al. | |
| 2021/0216822 A1* | 7/2021 | Paik | G16H 15/00 |
| 2021/0225512 A1* | 7/2021 | Himeno | G06F 16/245 |

OTHER PUBLICATIONS

International Search Report of PCT/US2023/061179, mailed May 8, 2023.
Anonymous "Second Opinion-The first real-time dental Al platform that automatically detects numerous conditions in dental x-rays to give dentists a second set of eyes for superior radiologic accuracy", Pearl, Inc. (2021), 4 pgs, https://www.hellopearl.com/products/second-opinion, obtained Sep. 1, 2022.
Radlogics, Inc., "FDA Warning Letter", Marcs-CMS 515599, Apr. 5, 2018, 4 pgs.

* cited by examiner

IMAGE ANALYSIS AND INSIGHT GENERATION

This application is a continuation of International Application No. PCT/US2023/061179, filed on Jan. 24, 2023, which claims the benefit of U.S. Provisional Application No. 63/393,116, filed on Jul. 28, 2022, and U.S. Provisional Application No. 63/302,799, filed on Jan. 25, 2022, the contents of which are each incorporated herein by reference in their entireties.

BACKGROUND

Medical professionals may rely on imaging techniques to develop a more informed diagnosis for a patient. Often, different medical professionals may have conflicting opinions on what the diagnosis may be. Additionally, due to human error, medical professionals may inadvertently overlook artifacts within an image, resulting in inaccurate reports. Manually generated reports may also take time to generate, longer time than may be demanded in an emergency situation. Further, conventional methods may utilize templates or rule-based algorithms, which may require manual input and may exclude artifacts not specified in the template or algorithm. Additionally, conventional methods may not allow for a user to communicate with the system in a conversational manner that aids in decision making. Thus, a need exists for improved radiological techniques and systems that afford medical professionals increased accuracy and efficiency over existing technologies.

BRIEF DESCRIPTION OF THE DRAWINGS

Various embodiments in accordance with the present disclosure will be described with reference to the drawings, in which.

DETAILED DESCRIPTION

Figure 1:
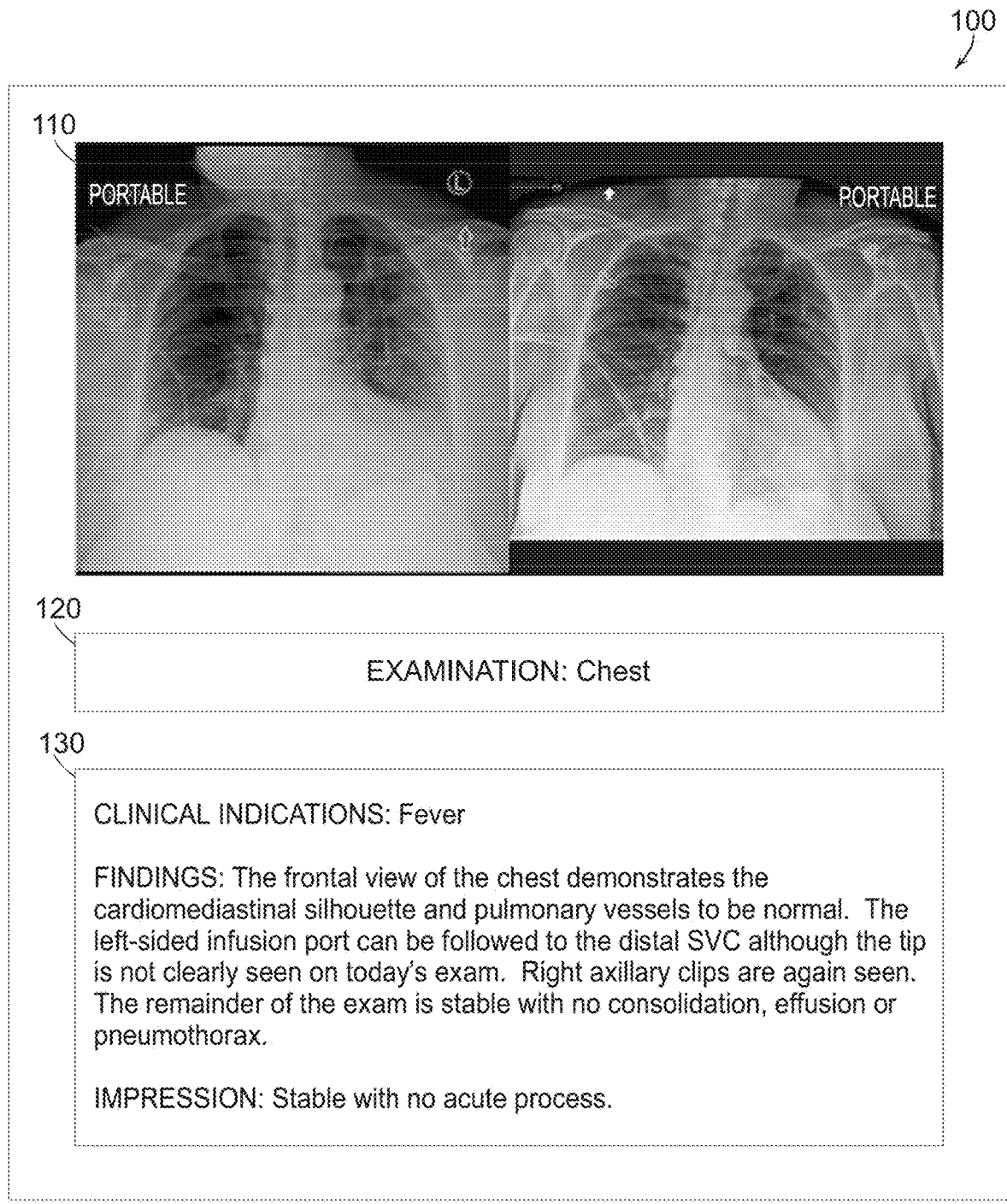
FIG. 1 illustrates an example interface that can be used to implement aspects of the various embodiments.

In the following description, various embodiments will be described. For purposes of explanation, specific configurations and details are set forth in order to provide a thorough understanding of the embodiments. However, it will also be apparent to one skilled in the art that the embodiments may be practiced without the specific details. Furthermore, well-known features may be omitted or simplified in order not to obscure the embodiment being described.

Medical imaging, in accordance with an exemplary embodiment, may include but is not limited to, techniques related to X-rays, computerized tomography (CT) scans, magnetic resonance imaging (MRI), nuclear medicine imaging positron-emission tomography (PET), and ultrasound. Medical imaging may also refer to any imaging-based techniques used to observe a human internally, such as techniques used in colonoscopies and endoscopies for example. Such medical imaging may provide information about physical issues related to a patient that are not readily visible to the human eye. However, given demanding schedules and/or limited personnel, it may be hours until a medical professional has time to analyze the image and generate a report related to the image. In such cases, the patient's condition may rapidly change while waiting for results to be read by the medical professional. For example, it may take hours for a medical professional working in gastroenterology to provide a consultation for a medical professional working in the emergency room. While the professional in the emergency room waits for the consult, the patient's condition may have since deteriorated. Further, one professional's opinion may differ from another professional's, or a professional may inadvertently overlook important artifacts which may be present in the image. As such, manually generated medical reports may not capture important details with a high degree of accuracy or integrity.

In accordance with an exemplary embodiment, an input image, such as an image obtained through the use of medical imaging techniques, may be received. A request for at least one insight related to the input image may also be received. The input image may be analyzed to detect one or more anomalies present in the input image. At least one neural network may be utilized to infer information associated with the input image. A plurality of reports related to the input image may be generated based, at least in part, upon the inferred information, wherein each of the plurality of reports have at least one associated metric.

In accordance with another exemplary embodiment, an input image may be received. Using a machine learning model, at least one inference associated with the image may be generated. A first output may be provided for display based, at least in part, upon the at least one inference. At least one interaction with the first output may be received. At least one second output may be provided for display in response to the received at least one interaction.

In accordance with yet another exemplary embodiment, a machine learning model may be trained on a set of training data, wherein the set of training data includes individual token values and one or more groupings of the individual token values. An input image can be received and analyzed, using the trained machine learning model. An output associated with the analyzed input image can be received or generated. At least a first subset of data received in the output can be sampled, wherein a second subset of data in the output is excluded from the sampling. A report associated with the input image can be generated based, at least in part, upon the sampled first subset of data.

FIG. 1 illustrates an example interface 100 that can be used to implement aspects of the various embodiments. As shown in FIG. 1, a medical image or a set of medical images 110 may be provided as an input. As explained above, medical imaging, in accordance with an exemplary embodiment may include, but is not limited to, techniques related to X-rays, computerized tomography (CT) scans, computerized axial tomography (CAT) scans, magnetic resonance imaging (MRI), nuclear medicine imaging positron-emission tomography (PET), and ultrasound. Medical imaging may also refer to any imaging-based techniques used to observe a human internally, such as techniques used in colonoscopies and endoscopies for example. Such medical imaging may provide information about physical issues related to a patient that are not readily visible to the human eye.

In accordance with an exemplary embodiment, the medical image(s) 110 may be provided along with a request, such as whether a professional would like a detailed report related to the image(s), or whether the professional's predicted diagnosis is accurate. Artificial intelligence may be utilized, in accordance with one or more embodiments, to help analyze an image and provide an interpretation of the image, in addition to validating a professional's opinion, among other such options. As described and/or referred to herein, artificial intelligence may include, but is not limited to, the use of machine learning, including unsupervised machine learning, semi-supervised or reinforcement machine learning, or supervised machine learning as may be applicable. Machine learning, as described and/or referred to herein, may include the use of neural networks and deep learning.

As shown in FIG. 1, the system may be able to automatically identify that the input image(s) represent an examination of the chest, as shown in the indication box 120. In cases where the image may not be as clear or the system cannot determine, with at least a threshold level of confidence, what the examination pertains to, the system may request additional input for clarifying information. In accordance with an exemplary embodiment, machine learning may be utilized to analyze an input image, such as a scan obtained through medical imaging, to detect any anomalies that may be present in a scan. In some exemplary embodiments, the input image may be compared against training data including historical data, image data, and text data, among other such options. Historical data may include various types of medical reports and associated medical images, including scans that are considered to be "healthy," or scans that have associated anomalies. In some embodiments, healthy scans may be excluded from the set of training data to minimize how much stored data is required to train a model. In such cases, the model may still operate with high accuracy, while increasing a computing device's processing speed. Training data, in at least some exemplary embodiments, may also include image data corresponding to items, such as items which may contribute to detection of an anomaly. For example, a child may have consumed a button or a coin. Images of a button or coin may be utilized as training data to help provide a potential diagnosis of a detected button or coin in an input image of the child. In some embodiments, an outline of an item may be compared against the training data to determine what the potential source of the anomaly may be, as imaging may not provide clear information about features present on the anomalous object.

As shown at 130, a report may be generated, in accordance with an exemplary embodiment, based on the analysis. For example, if an initial request was to check for a diagnosis, then the report may indicate whether that diagnosis was found during the analysis. Alternatively, if the initial request was to provide a summary of potential anomalies or to generate a diagnosis, the report may be provided as a response to the request including information pertinent to the request. In accordance with an exemplary embodiment, a user may also prompt the system to provide a description or explanation pertaining to an identified portion of the input image. In this way, the user can essentially have a conversational relationship with the computing system to better inform the user's decisions pertaining to the image. In this example of FIG. 1, the system was requested to provide a report or summary of any findings based on the input image(s) 110. As shown, the system was able to generate findings based on clinical indications. Clinical indications, such as a fever, may be provided by a professional so that the system may have additional context information when generating a report. In this way, the summarized findings can be tailored and may provide a more accurate representation of any findings and other considerations a professional should be concerned about. In addition to findings, the system may be able to provide a summarized impression indicating whether immediate action is required or if a patient is in stable condition. In at least some embodiments, the report may be generated utilizing an encoder/decoder framework, such as through a transformer model including, but not limited to, a Bidirectional and Auto-Regressive (BART) model, a Bidirectional Encoder Representations from Transformers (BERT) model, or a large transformer-based language model such as a Generative Pre-trained Transformer (GPT) model.

As described herein, training data may include outputs from multiple types of models including, but not limited to, a trained image model, a trained text-based model, and a model trained on historical data, such as a plurality of medical reports. The training data in the reports may account for medical issues which may be difficult to initially diagnose. For example, a report corresponding to a more complicated assessment may be utilized to help the model understand such complex cases. A patient, for example, may have a small pneumothorax in one portion of an image, but the model may be able to identify a mediastinal shift of the trachea that an ordering medical professional may have initially missed. In this case, the professional may have ordered the image to confirm the pneumothorax and so their attention may be attuned to only that portion of the image. As such, the professional may have missed the mediastinal shift because they did not realize there was an issue to look out for with the trachea. Certainly, other medical personnel may catch the shift, but there would not be a reason to call for a consultation on the trachea if the initial professional did not catch that issue. As such, by utilizing the trained model as described herein, a more comprehensive assessment of a patient's imaging may be provided. After the system has identified the mediastinal shift, a user may ask the system follow-up questions related to the shift, such as to generate additional reports related to that specific portion of the image, or by selecting other reports that may provide alternative explanations for the issue. In this way, the user can have a conversation with the computing system, as they would with any other professional in the medical field, to get a better understanding of the issue. Individual reports may be provided with certainty values or other metrics, indicating a certainty of confidence in the accuracy of a report. A user may look at the certainty value for a given report and determine how much weight should be given to that report when generating their overall diagnosis. Other metrics, in accordance with exemplary embodiments, may include an average confidence score across token values, a maximum confidence score for a single report, a minimum confidence score for a single report, a standard deviation of the confidence score(s), and a number of foci of highlights in a report/image pairing, among other such metrics.

Conventionally, a model may be optimized to reduce loss as much as possible. For example, a model may be optimized to not be overfit to reduce loss. However, in specific contexts such as in the medical field, it may be beneficial to consider additional data points which may otherwise be excluded due to the lack of certainty. For example, it may be beneficial to intentionally overfit the model to make the model more confident about predications, even though this may result in worse loss, because the overall clinical performance is better. In this example, the model may only be required to train on memorized passages of words instead of specific words or syllables, so the model can spend more resources analyzing clinical details pertinent to a request instead of determining how to present a set of words summarizing the analysis.

In accordance with an exemplary embodiment, in cases where a set of reports are being generated for a given input image, a histogram may be generated and provided for presentation, along with a certainty of accuracy. A histogram may be a graph with a series of peaks, wherein individual peaks may be associated with possible frequency distributions. A conventional system may focus only on a single peak corresponding to the most accurate output, having the highest frequency of accuracy. However, in certain instances, such as with the practice of medicine, it may be beneficial to analyze smaller peaks in case there are additional or alternative diagnoses that should be considered. For example, in the medical field, it is common for different medical professionals to disagree on a finding in an image. In accordance with one or more exemplary embodiments, a user may click on one or more of the peaks and view other possible diagnoses as presented in the report, or as provided in the form of labels on the image. In this way, a user may have a representation of what numerous professionals would predict for the image (e.g., 100 professionals for 100 generated reports), giving the user a more comprehensive overview of predictions. If the histogram only has one peak, then a user can feel confident in their diagnosis. However, if there are numerous peaks (e.g., such as two or more), a user may determine that additional information is needed to comfortably commit to a diagnosis, or the user may suggest that each peak is a representative alternative of what the underlying condition could be. This example is not intended to be limiting, and other forms of indications may be provided.

Figure 2:
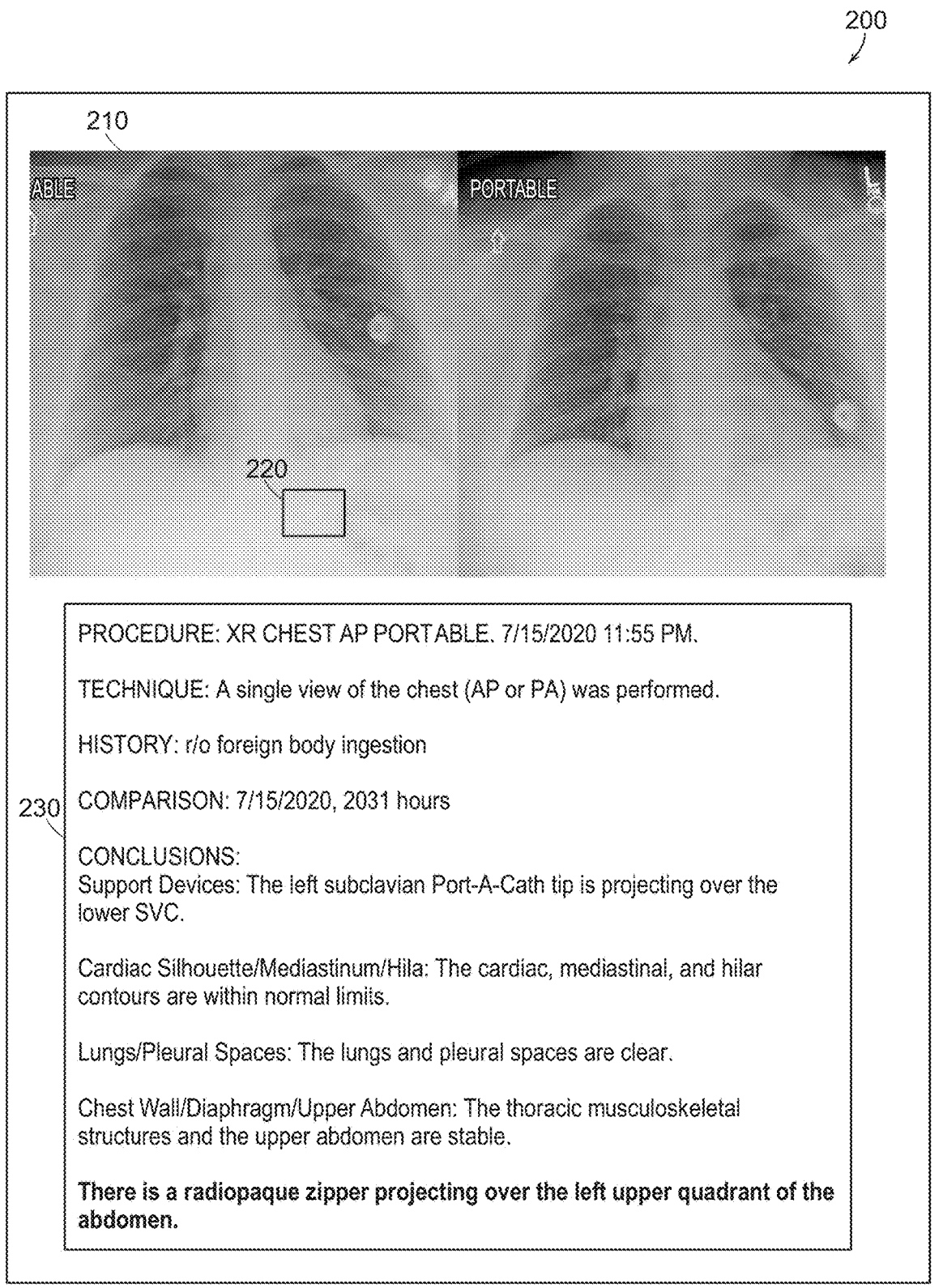
FIG. 2 illustrates another example interface that can be utilized to implement aspects of the various embodiments.

FIG. 2 illustrates another exemplary interface 200 that can be utilized to implement aspects of the various embodiments. As shown in this example, one or more medical image(s) 210 may be provided to a computing system for analysis. The type of procedure, technique, history, and potential indications, among other such information, may be provided as context information for the computing system to consider. In accordance with one or more techniques described herein, the computing system may utilize artificial intelligence to analyze the input image(s) 210 and generate a report 230, including the context information and conclusions and indications determined by the computing system. Alternatively or additionally, a user may be able to ask the computing system to look at a specific detail as many times as they want, such that the computing system may provide numerous results which may differ with each iteration. By doing so, the user and computing system have established a conversational approach to helping the user create an overall diagnosis of what the image is showing. As shown in FIG. 2, the computing system was able to determine that "there is a radiopaque zipper projecting over the left upper quadrant of the abdomen." In other words, the system detected a foreign object 220 in the body, and included that finding in the report 230 to alert a reader of the report. Based on this information, the reader may then take necessary action, such as ordering a scan for that specific area of the body, to ensure that the patient is not facing other issues apart from the catheter. The user may additionally manually highlight or otherwise select a portion of the report to formulate a next question for the computing system, as an indicator to the computing system that their next question is related to the highlighted portion of the report. Similarly, the user may be able to highlight or otherwise select a portion of the input image to indicate to the computing system that their next question relates to the portion of the input image. In accordance with an alternative embodiment, a user may be able to interact with a portion of the input image, and the system can automatically highlight corresponding portions of a generated report that may relate to the interacted portion of the input image. The user may also ask the system to generate a report related to a specific condition. For example, while the report in FIG. 2 notes a radiopaque zipper, the user may ask about whether the system sees any infection that could be present in the patient. In accordance with an example embodiment, the system may also generate a recommendation for how to proceed when an anomaly is detected. Recommendations may include suggestions for ordering additional imaging for specified areas or requesting consultations with specific providers regarding specific issues that were detected.

Figure 3:
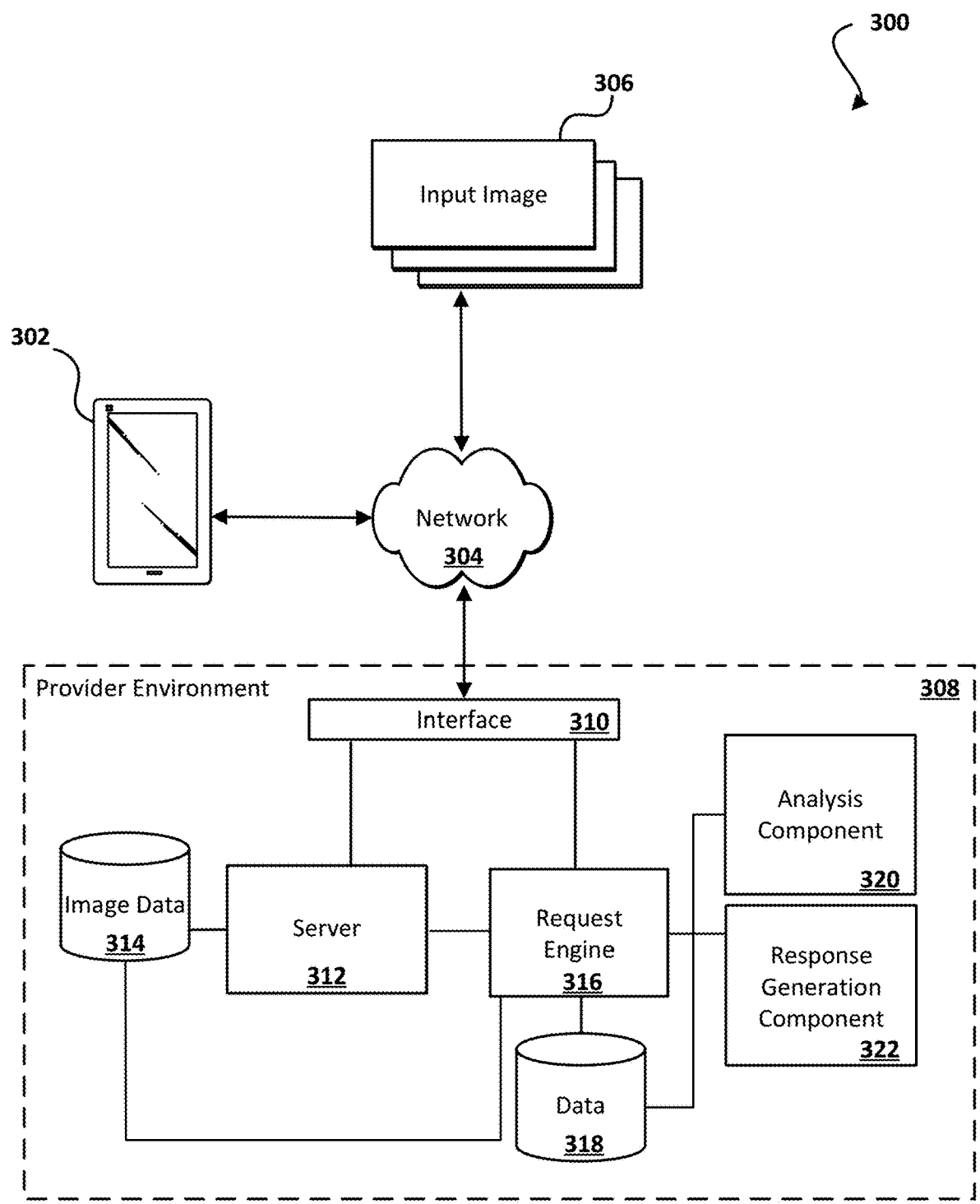
FIG. 3 illustrates an example system that can be utilized to implement one or more aspects of various embodiments.

As shown in the exemplary system 300 of FIG. 3, a user may be able to use a client device 302 to submit a request including a query related to an input image 306 received in an environment, across at least one network 304. The request can be received by a user, such as a medical professional, submitting a query through a provider environment 308. A query may be submitted through any suitable method (e.g., a text query, a voice request, image-based query, etc.). In this exemplary embodiment, a query may include a request to confirm a diagnosis related to an input image, or a request for a report including any anomalies that may be present in an input image, among other such queries. Although a portable computing device (e.g., an electronic book reader, smart phone, or tablet computer) is shown as the client device 302, it should be understood that any electronic device capable of receiving, determining, and/or processing input can be used in accordance with various embodiments discussed herein, where the devices can include, for example, desktop computers, notebook computers, personal data assistants, video gaming consoles, television set top boxes, wearable computers (i.e., smart watches and glasses) and portable media players, among others.

The at least one network 304 can include any appropriate network, such as may include the Internet, an Intranet, a local area network (LAN), a cellular network, a Wi-Fi network, and the like. The request can be sent to an appropriate provider environment 308, which can provide one or more services, systems, or applications for processing such requests. The provider can be any source of digital or electronic content, as may include a website provider, a hospital with electronic records, a content distributor, and the like.

In this example, the request is received by a network interface layer 310 of the provider environment 308. The network interface layer can include any appropriate components known or used to receive requests from across a network, such as may include one or more application programming interfaces (APIs) or other such interfaces for receiving such requests. The network interface layer 310 might be owned and operated by the provider, or leveraged by the provider as part of a shared resource or "cloud" offering. The network interface layer can receive and analyze the request from the client device 302, and cause at least a portion of the information in the request to be directed to an appropriate system or service, such as a server 312 (e.g., a Web server or application server), among other such options. In the case of webpages, for example, at least one server 312 might be used to generate code and send content for rendering the requested Web page. In cases where processing is to be performed, such as to generate results in response to a request, perform an operation on a user input, verify information for the request, etc., information might also be directed to at least one other server for processing, for example a request engine 316. The servers or other components of the environment might access one or more data stores, such as an image data store 314 that contains image data, as a form of training data, that can be utilized by a request engine 316. In some exemplary embodiments, an image data store 314 may additionally contain corresponding reports related to image data which may be utilized as training data.

The request engine 316 may receive the request from the server and may determine one or more responses to the request. In at least some embodiments, the request engine 316 may consider information provided by an analysis component 320 and provide analytics to a response generation component 322. The analysis component 320 may utilize one or more artificial intelligence techniques, including machine learning, to analyze an input image and determine any anomalies that may be present in the input image. For example, training data may be utilized to predict and/or identify any anomalies that may be present in the input image. Additionally, an analysis component may be able to consider data, such as data present in a manually-generated report, and determine whether the report is accurate in view of an input image. The response generation component 322 may generate a report or indication, in view of the results of the analysis component, to provide to the request engine 316. For example, the response generation component 322 may utilize a language model to generate a report or provide an indication as to whether a diagnosis is accurate. The request engine 316 may interface with the analysis component 320 and the response generation component 322 through any suitable manner in order to perform the functionality described herein. Data store 318 may contain additional training data, such as language or textual training data and historical training data, language models, and/or results from the analysis component 320 and the response generation component 322. In at least some exemplary embodiments, the results from the analysis component 320 and/or the response generation component 322 may be utilized as training data for use with future requests.

Figure 4:
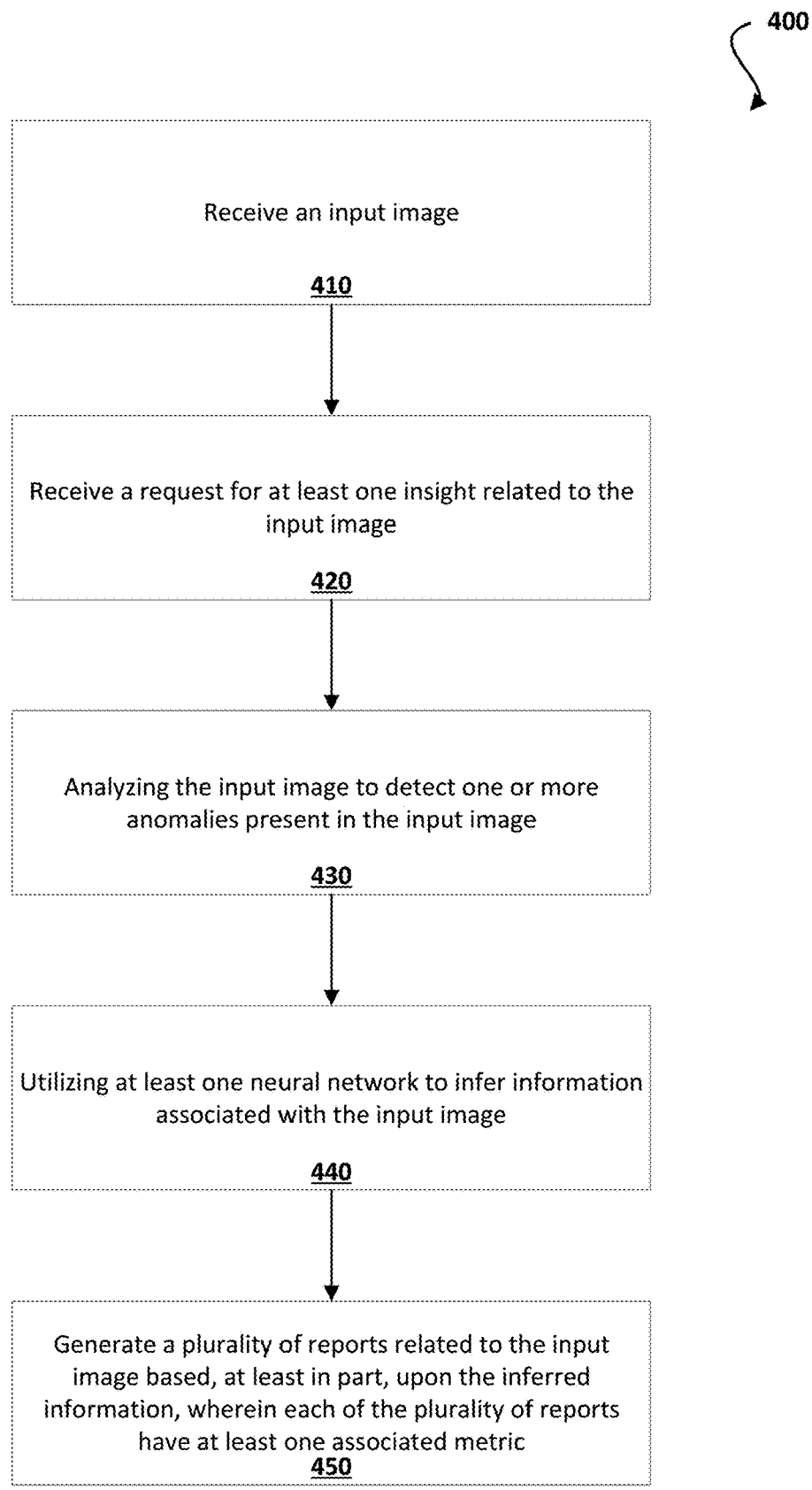
FIG. 4 illustrates an example method that can be utilized in accordance with various embodiments.

FIG. 4 illustrates an exemplary method 400 that can be utilized in accordance with various embodiments. It should be understood that for any process herein there can be additional, fewer, or alternative steps performed in similar or alternative orders, or in parallel, within the scope of the various embodiments unless otherwise specifically stated.

In this exemplary embodiment, an input image may be received 410. In some examples, the input image may be a medical image obtained through radiology. In other examples, the input image may correspond to video data, such as video data obtained during a procedure, or other image and video data unrelated to the medical field. A request for at least one insight related to the input image may also be received 420. For example, a user, including but not limited to a medical professional, may submit a request for a report summarizing any findings associated with the input image. The medical report, in at least some exemplary embodiments, may be automatically generated, such as by using artificial intelligence techniques. The input image may be analyzed to detect one or more anomalies that may be present in the input image 430. For example, using machine learning or other artificial intelligence techniques, the input image may be analyzed. An underlying algorithm may be trained on one or more sets of training data, including but not limited to language models, image models, and historical data such as existing radiological data. Utilizing at least one neural network, information associated with the input image may be inferred 440. Based at least in part upon the inferred information, a plurality of reports may be generated 450.

Each of the plurality of reports, in at least some embodiments, may have an associated level of confidence or metric, corresponding to an average level of certainty with a given report. For example, one report may have a high level of confidence in certainty (e.g., greater than a threshold level of certainty) such that it would be more likely than not an accurate report and diagnosis. Individual reports may be provided with certainty values or other metrics, indicating a certainty of confidence in the accuracy of a report. A user may look at the certainty value for a given report and determine how much weight should be given to that report when generating their overall diagnosis. Other metrics, in accordance with exemplary embodiments, may include an average confidence score across token values, a maximum confidence score for a single report, a minimum confidence score for a single report, a standard deviation of the confidence score(s), and a number of foci of highlights in a report/image pairing, among other such metrics. In using such confidence scores and/or metrics, a user may feel confident basing a diagnosis off of that report. In other cases, a report may have a fairly high level of certainty (e.g., within a range of certainty that is below the threshold level of certainty, but above a minimum level of certainty). In those cases, a user may look at other reports that were generated to obtain a better understanding of what is going on in the input image. For example, a doctor may receive reports related to the same image, and each related report may provide a different interpretation of the image. Based on at least a subset of the interpretations, a doctor may provide a more comprehensive diagnosis and/or order potential follow-up tests related to the potential diagnosis/diagnoses. In some embodiments, a generated report may be utilized by a trained professional to obtain a better understanding of the image, or to determine whether there are any anomalies that the professional may have missed in their initial diagnosis. The plurality of reports, in accordance with an example embodiment, may be provided in a histogram such that each datapoint on the histogram corresponds to an individual report of a determined level of certainty. By presenting the reports to the user in the form of a histogram, a user may have a better understanding of the various findings in the reports, and can determine whether they should base their opinion on individual reports.

Figure 5:
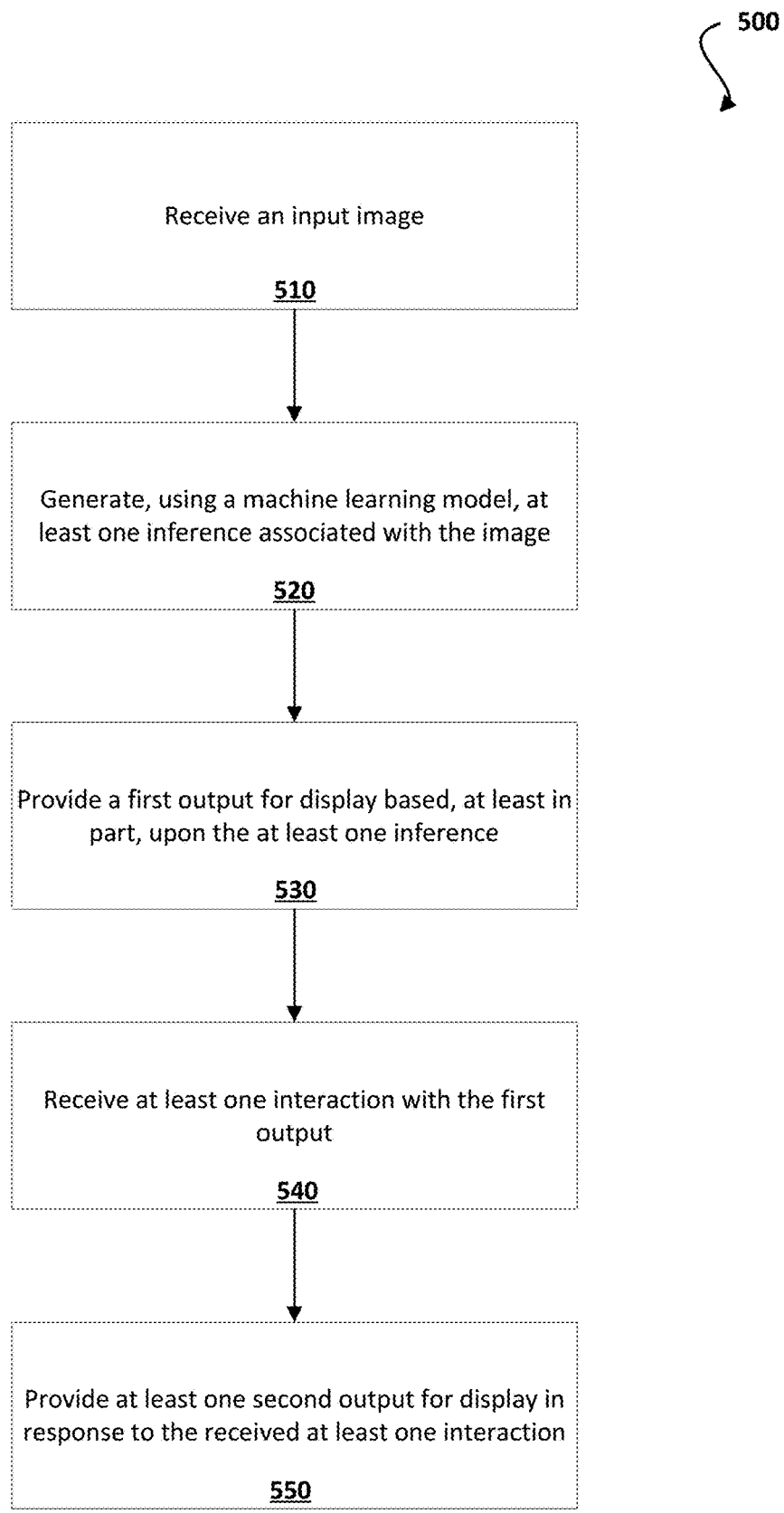
FIG. 5 illustrates another example method that can be utilized in accordance with various embodiments.

FIG. 5 illustrates another exemplary method 500 that can be utilized in accordance with various embodiments. It should be understood that for any process herein there can be additional, fewer, or alternative steps performed in similar or alternative orders, or in parallel, within the scope of the various embodiments unless otherwise specifically stated.

In this exemplary embodiment, an input image may be received 510. In some examples, the input image may be a medical image obtained through radiology. In other examples, the input image may correspond to video data, such as video data obtained during a procedure, or other image and video data unrelated to the medical field. A machine learning algorithm may be used, in accordance with one or more embodiments, to generate at least one inference associated with the input image 520. The input image may be analyzed to detect one or more anomalies that may be present in the input image. For example, using machine learning or other artificial intelligence techniques, the input image may be analyzed. An underlying algorithm may be trained on one or more sets of training data, including but not limited to language models, image models, and existing radiological data. Based at least in part upon the inference, a first output may be provided for display 530. For example, a set of reports summarizing one or more findings in the input image may be provided for display, in response to the initial query. In this example, findings may correspond to potential information that could contribute to a medical diagnosis.

At least one interaction with the first output may be received 540. In accordance with an exemplary embodiment, a user may interact with one or more of the generated reports, such as by highlighting a feature in the report or input image, asking follow-up questions, or asking the system to regenerate a set of reports in view of the highlighted feature(s), among other such interactions. In at least some exemplary embodiments, features present in the input image may be linked to one or more terms, such that a detected anomaly links to a corresponding explanation. If a user hovers over or clicks on a detected anomaly, a corresponding section of text may be highlighted or otherwise provided in a prominent display to the user. Similarly, if a user hovers over or clicks on a section of text, an indication may be provided in the image, such as a box surrounding the anomaly. Such linking may be performed automatically, through the use of artificial intelligence techniques. The system may then provide at least one second output for display in response to the received at least one interaction 550. Based on the second output, a user may be able to use information provided in the second output to better understand any findings in the generated reports, such as to make a better medical diagnosis with a more comprehensive overview and analysis of the input image.

Figure 6:
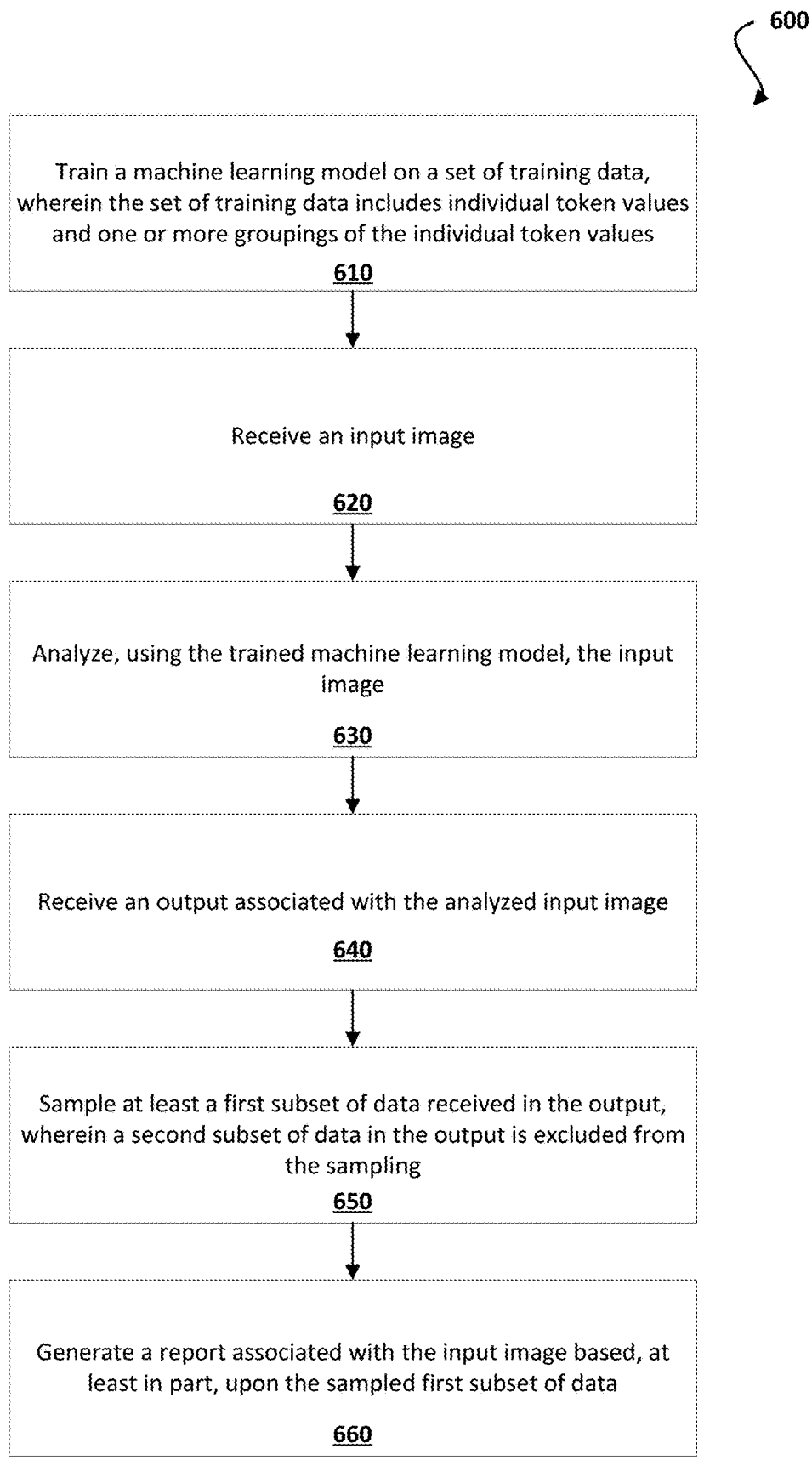
FIG. 6 illustrates another example method that can be utilized in accordance with various embodiments.

FIG. 6 illustrates another exemplary method 600 that can be utilized in accordance with various embodiments. It should be understood that for any process herein there can be additional, fewer, or alternative steps performed in similar or alternative orders, or in parallel, within the scope of the various embodiments unless otherwise specifically stated.

In this exemplary embodiment, a machine learning model may be trained on at least one set of training data, wherein the at least one set of training data includes individual token values and one or more groupings of the individual token values 610. For example, the machine learning model may train on multiple words or syllables at a time, with each syllable or group of words corresponding to a token value, in contrast to conventional models that prevent memorization of words and syllables due to the potential for overfitting the model. In cases where a model is overfit, it can be easily apparent that text generated by the overfit model was in fact generated by the computing system instead of sounding like natural language. In some example embodiments, token values may correspond to individual pixel values of an image.

An input image may be received 620. In some examples, the input image may be a medical image obtained through radiology. In other examples, the input image may correspond to video data, such as video data obtained during a procedure, or other image and video data unrelated to the medical field. Using the trained machine learning model, the input image may be processed or analyzed 630. An output associated with the analyzed input image may be received 640. In accordance with an exemplary embodiment, the output may include a probability distribution of generated text. In at least some exemplary embodiments, the probability distribution may be overfit to the training data. As mentioned elsewhere herein, overfitting a model may cause undesirable results in conventional systems, including text that reads unnaturally to a human. At least a first subset of data received in the output may be sampled, wherein a second subset of data in the output is excluded from the sampling 650. For example, at least some of the results of the probability distribution may be excluded from sampling based on a threshold value applied against the results. While examples described herein refer to a probability distribution, other types of distributions may be used in accordance with the various embodiments. A report associated with the input image may be generated based, at least in part, upon the sampled first subset of data 660. By generating the report in this way, the report may read more naturally to a human even after the model has been overfit. In terms of overfitting, text can be overfit but not pixels, or pixels can be overfit and not text.

Figure 7:
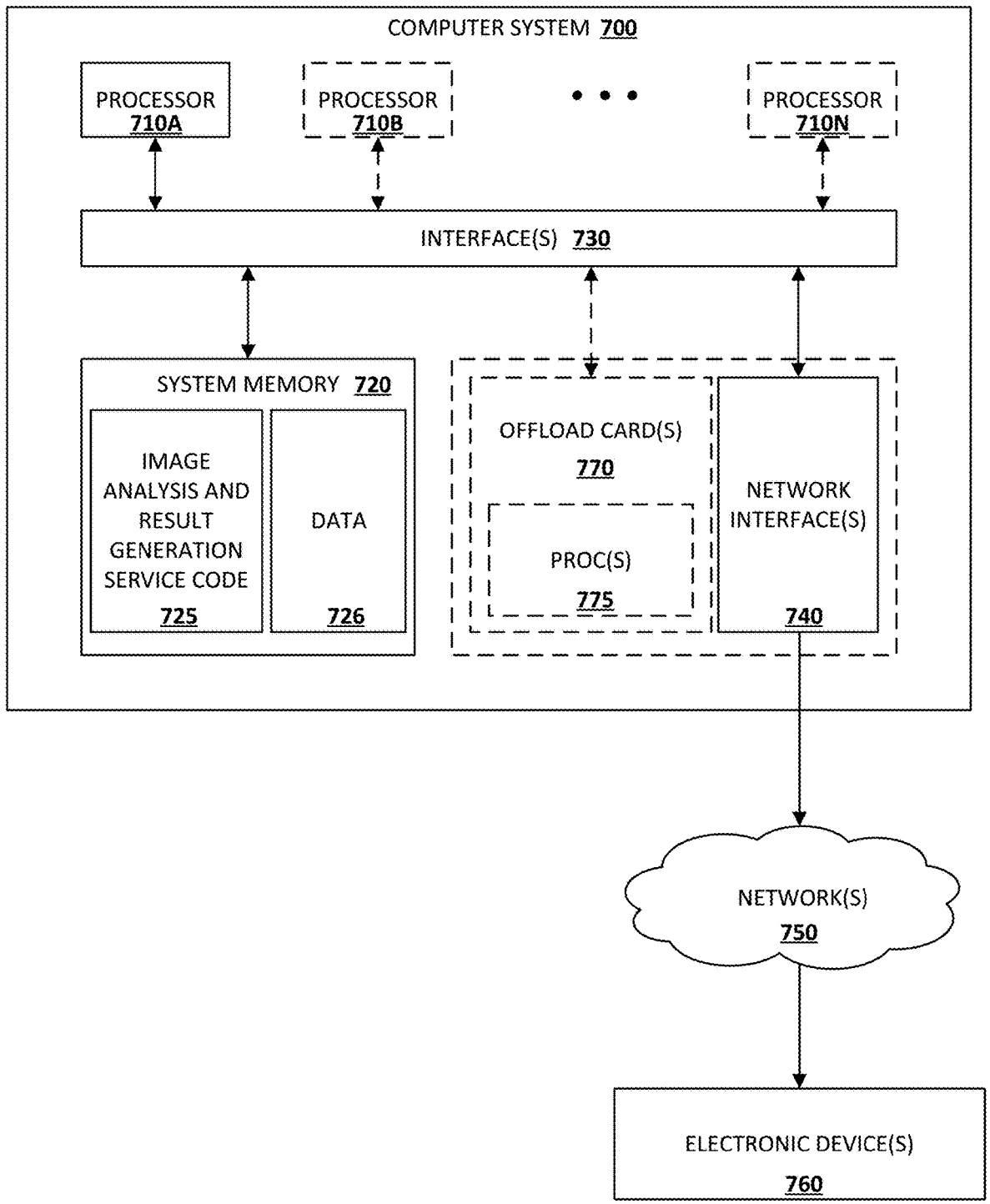
FIG. 7 illustrates a system that can be used to implement at least a portion, or all of the techniques described herein, according to some embodiments.

In some embodiments, a system that implements a portion or all of the techniques described herein may include a general-purpose computer system that includes or is configured to access one or more computer-accessible media, such as the computer system 700 illustrated in FIG. 7. In the illustrated embodiment, a computer system 700 includes one or more processors 710A-710N coupled to a system memory 720 via an input/output (I/O) interface 730. The computer system 700 further includes a network interface 740 coupled to I/O interface 730. While FIG. 7 shows a computer system 700 as a single computing device, in various embodiments a computer system 700 may include one computing device or any number of computing devices configured to work together as a single computer system 700.

In various embodiments, a computer system 700 may be a uniprocessor system including one processor 710A, or a multiprocessor system including several processors 710A-710N (e.g., two, four, eight, or another suitable number). Processors 710A-710N may be any suitable processors capable of executing instructions. For example, in various embodiments, processors 710A-710N may be general-purpose or embedded processors implementing any of a variety of instruction set architectures (ISAs). In multiprocessor systems, each of processors 710A-710N may commonly, but not necessarily, implement the same ISA.

System memory 720 may store instructions and data accessible by processor(s) 710A-710N. In various embodiments, system memory 720 may be implemented using any suitable memory technology, such as random-access memory (RAM), static RAM (SRAM), synchronous dynamic RAM (SDRAM), nonvolatile/Flash-type memory, or any other type of memory. In the illustrated embodiment, program instructions and data implementing one or more desired functions, such as those methods, techniques, and data described above are shown stored within system memory 720 as image analysis and result generation service code 725 and data 726.

In one embodiment, I/O interface 730 may be configured to coordinate I/O traffic between processor(s) 710A-710N, system memory 720, and any peripheral devices in the device, including network interface 740 or other peripheral interfaces. In some embodiments, I/O interface 730 may perform any necessary protocol, timing or other data transformations to convert data signals from one component (e.g., system memory 720) into a format suitable for use by another component (e.g., processor(s) 710A-710N). In some embodiments, I/O interface 730 may include support for devices attached through various types of peripheral buses, such as a variant of the Peripheral Component Interconnect (PCI) bus standard or the Universal Serial Bus (USB) standard, for example. In some embodiments, the function of I/O interface 730 may be split into two or more separate components, such as a north bridge and a south bridge, for example. Also, in some embodiments some or all of the functionality of I/O interface 730, such as an interface to system memory 720, may be incorporated directly into processor(s) 710A-710N.

A network interface 740 may be configured to allow data to be exchanged between a computer system 700 and other devices 760 attached to a network or networks 750. In various embodiments, a network interface 740 may support communication via any suitable wired or wireless general data networks, such as types of Ethernet network, for example. Additionally, a network interface 740 may support communication via telecommunications/telephony networks such as analog voice networks or digital fiber communications networks, via storage area networks (SANs) such as Fibre Channel SANs, or via I/O any other suitable type of network and/or protocol.

In some embodiments, a computer system 700 includes one or more offload cards 770 (including one or more processors 775, and possibly including the one or more network interfaces 740) that are connected using an I/O interface 730 (e.g., a bus implementing a version of the Peripheral Component Interconnect Express (PCI-E) standard, or another interconnect such as a QuickPath interconnect (QPI) or UltraPath interconnect (UPI)). For example, in some embodiments the computer system 700 may act as a host electronic device (e.g., operating as part of a hardware virtualization service) that hosts compute instances, and the one or more offload cards 770 execute a virtualization manager that can manage compute instances that execute on the host electronic device. As an example, in some embodiments the offload card(s) 770 can perform compute instance management operations such as pausing and/or un-pausing compute instances, launching and/or terminating compute instances, performing memory transfer/copying operations, etc. These management operations may, in some embodiments, be performed by the offload card(s) 770 in coordination with a hypervisor (e.g., upon a request from a hypervisor) that is executed by the other processors 710A-710N of the computer system 700. However, in some embodiments the virtualization manager implemented by the offload card(s) 770 can accommodate requests from other entities (e.g., from compute instances themselves), and may not coordinate with (or service) any separate hypervisor.

In some embodiments, system memory 720 may be one embodiment of a computer-accessible medium configured to store program instructions and data as described above. However, in other embodiments, program instructions and/or data may be received, sent, or stored upon different types of computer-accessible media. Generally speaking, a computer-accessible medium may include non-transitory storage media or memory media such as magnetic or optical media, e.g., a disk or DVD/CD coupled to a computer system 700 via I/O interface 730. A non-transitory computer-accessible storage medium may also include any volatile or non-volatile media such as RAM (e.g., SDRAM, double data rate (DDR) SDRAM, SRAM, etc.), read only memory (ROM), etc., that may be included in some embodiments of a computer system 700 as system memory 720 or another type of memory. Further, a computer-accessible medium may include transmission media or signals, such as electrical, electromagnetic, or digital signals, conveyed via a communication medium such as a network and/or a wireless link, such as may be implemented via a network interface 740.

Figure 8:
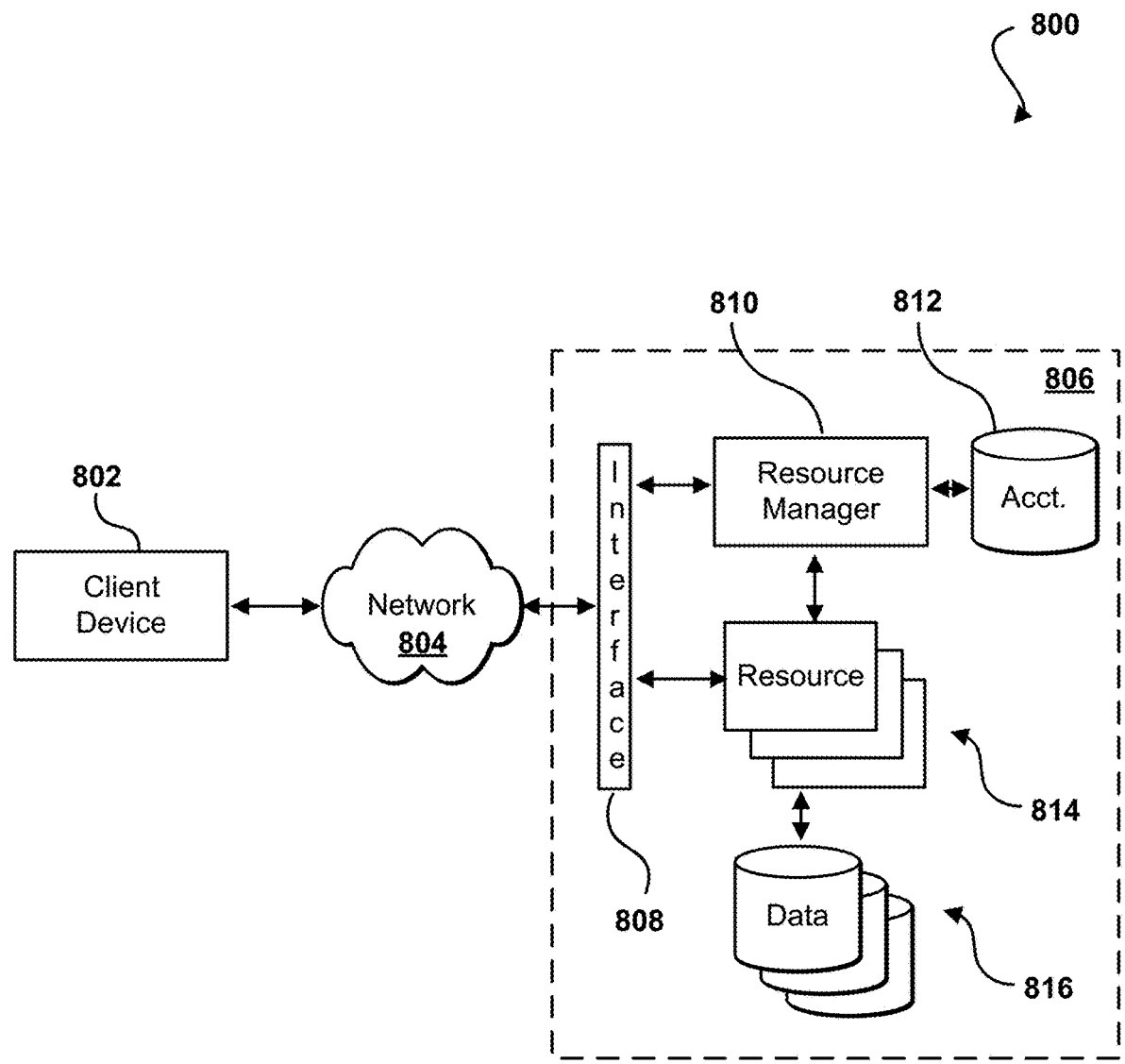
FIG. 8 illustrates components of another example environment in which aspects of various embodiments can be implemented.

FIG. 8 illustrates an exemplary environment 800 in which aspects of the various embodiments can be implemented. In this example a user is able to utilize a client device 802 to submit requests across at least one network 804 to a multi-tenant resource provider environment 806. The client device can include any appropriate electronic device operable to send and receive requests, messages, or other such information over an appropriate network and convey information back to a user of the device. Examples of such client devices include personal computers, tablet computers, smart phones, notebook computers, and the like. The at least one network 804 can include any appropriate network, including an intranet, the Internet, a cellular network, a local area network (LAN), or any other such network or combination, and communication over the network can be enabled via wired and/or wireless connections. The resource provider environment 806 can include any appropriate components for receiving requests and returning information or performing actions in response to those requests. As an example, the provider environment might include Web servers and/or application servers for receiving and processing requests, then returning data, Web pages, video, audio, or other such content or information in response to the request.

In various embodiments, the provider environment may include various types of resources that can be utilized by multiple users for a variety of different purposes. As used herein, computing and other electronic resources utilized in a network environment can be referred to as "network resources." These can include, for example, servers, databases, load balancers, routers, and the like, which can perform tasks such as to receive, transmit, and/or process data and/or executable instructions. In at least some embodiments, all or a portion of a given resource or set of resources might be allocated to a particular user or allocated for a particular task, for at least a determined period of time. The sharing of these multi-tenant resources from a provider environment is often referred to as resource sharing, Web services, or "cloud computing," among other such terms and depending upon the specific environment and/or implementation. In this example the provider environment includes a plurality of resources 814 of one or more types. These types can include, for example, application servers operable to process instructions provided by a user or database servers operable to process data stored in one or more data stores 816 in response to a user request. As known for such purposes, the user can also reserve at least a portion of the data storage in a given data store. Methods for enabling a user to reserve various resources and resource instances are well known in the art, such that detailed description of the entire process, and explanation of all possible components, will not be discussed in detail herein.

In at least some embodiments, a user wanting to utilize a portion of the resources 814 can submit a request that is received to an interface layer 808 of the provider environment 806. The interface layer can include application programming interfaces (APIs) or other exposed interfaces enabling a user to submit requests to the provider environment. The interface layer 808 in this example can also include other components as well, such as at least one Web server, routing components, load balancers, and the like. When a request to provision a resource is received to the interface layer 808, information for the request can be directed to a resource manager 810 or other such system, service, or component configured to manage user accounts and information, resource provisioning and usage, and other such aspects. A resource manager 810 receiving the request can perform tasks such as to authenticate an identity of the user submitting the request, as well as to determine whether that user has an existing account with the resource provider, where the account data may be stored in at least one data store 812 in the provider environment. A user can provide any of various types of credentials in order to authenticate an identity of the user to the provider. These credentials can include, for example, a username and password pair, biometric data, a digital signature, or other such information. The provider can validate this information against information stored for the user. If the user has an account with the appropriate permissions, status, etc., the resource manager can determine whether there are adequate resources available to suit the user's request, and if so can provision the resources or otherwise grant access to the corresponding portion of those resources for use by the user for an amount specified by the request. This amount can include, for example, capacity to process a single request or perform a single task, a specified period of time, or a recurring/renewable period, among other such values. If the user does not have a valid account with the provider, the user account does not enable access to the type of resources specified in the request, or another such reason is preventing the user from obtaining access to such resources, a communication can be sent to the user to enable the user to create or modify an account, or change the resources specified in the request, among other such options.

Once the user is authenticated, the account verified, and the resources allocated, the user can utilize the allocated resource(s) for the specified capacity, amount of data transfer, period of time, or other such value. In at least some embodiments, a user might provide a session token or other such credentials with subsequent requests in order to enable those requests to be processed on that user session. The user can receive a resource identifier, specific address, or other such information that can enable the client device 802 to communicate with an allocated resource without having to communicate with the resource manager 810, at least until such time as a relevant aspect of the user account changes, the user is no longer granted access to the resource, or another such aspect changes.

The resource manager 810 (or another such system or service) in this example can also function as a virtual layer of hardware and software components that handles control functions in addition to management actions, as may include provisioning, scaling, replication, etc. The resource manager can utilize dedicated APIs in the interface layer 808, where each API can be provided to receive requests for at least one specific action to be performed with respect to the data environment, such as to provision, scale, clone, or hibernate an instance. Upon receiving a request to one of the APIs, a Web services portion of the interface layer can parse or otherwise analyze the request to determine the steps or actions needed to act on or process the call. For example, a Web service call might be received that includes a request to create a data repository.

An interface layer 808 in at least one embodiment includes a scalable set of user-facing servers that can provide the various APIs and return the appropriate responses based on the API specifications. The interface layer also can include at least one API service layer that in one embodiment consists of stateless, replicated servers which process the externally-facing user APIs. The interface layer can be responsible for Web service front end features such as authenticating users based on credentials, authorizing the user, throttling user requests to the API servers, validating user input, and marshalling or unmarshalling requests and responses. The API layer also can be responsible for reading and writing database configuration data to/from the administration data store, in response to the API calls. In many embodiments, the Web services layer and/or API service layer will be the only externally visible component, or the only component that is visible to, and accessible by, users of the control service. The servers of the Web services layer can be stateless and scaled horizontally as known in the art. API servers, as well as the persistent data store, can be spread across multiple data centers in a region, for example, such that the servers are resilient to single data center failures.

The various embodiments can be further implemented in a wide variety of operating environments, which in some cases can include one or more user computers or computing devices, which can be used to operate any of a number of applications. User or client devices can include any of a number of general purpose personal computers, such as desktop or laptop computers running a standard operating system, as well as cellular, wireless and handheld devices running mobile software and capable of supporting a number of networking and messaging protocols. Such a system can also include a number of workstations running any of a variety of commercially-available operating systems and other known applications for purposes such as development and database management. These devices can also include other electronic devices, such as dummy terminals, thin-clients, gaming systems and other devices capable of communicating via a network.

Most embodiments utilize at least one network that would be familiar to those skilled in the art for supporting communications using any of a variety of commercially available protocols, such as TCP/IP, FTP, UPnP, NFS, and CIFS. The network can be, for example, a local area network, a wide-area network, a virtual private network, the Internet, an intranet, an extranet, a public switched telephone network, an infrared network, a wireless network and any combination thereof. In embodiments utilizing a Web server, the Web server can run any of a variety of server or mid-tier applications, including HTTP servers, FTP servers, CGI servers, data servers, Java servers and business application servers. The server(s) may also be capable of executing programs or scripts in response requests from user devices, such as by executing one or more Web applications that may be implemented as one or more scripts or programs written in any programming language, such as Java®, C, C# or C++ or any scripting language, such as Perl, Python or TCL, as well as combinations thereof. The server(s) may also include database servers, including without limitation those commercially available from Oracle®, Microsoft®, Sybase® and IBM®.

The environment can include a variety of data stores and other memory and storage media as discussed above. These can reside in a variety of locations, such as on a storage medium local to (and/or resident in) one or more of the computers or remote from any or all of the computers across the network. In a particular set of embodiments, the information may reside in a storage-area network (SAN) familiar to those skilled in the art. Similarly, any necessary files for performing the functions attributed to the computers, servers or other network devices may be stored locally and/or remotely, as appropriate. Where a system includes computerized devices, each such device can include hardware elements that may be electrically coupled via a bus, the elements including, for example, at least one central processing unit (CPU), at least one input device (e.g., a mouse, keyboard, controller, touch-sensitive display element or keypad) and at least one output device (e.g., a display device, printer or speaker). Such a system may also include one or more storage devices, such as disk drives, optical storage devices and solid-state storage devices, such as random access memory (RAM) or read-only memory (ROM), as well as removable media devices, memory cards, flash cards, etc. Such devices can also include a computer-readable storage media reader, a communications device (e.g., a modem, a network card (wireless or wired), an infrared communication device) and working memory as described above. The computer-readable storage media reader can be connected with, or configured to receive, a computer-readable storage medium representing remote, local, fixed and/or removable storage devices as well as storage media for temporarily and/or more permanently containing, storing, transmitting and retrieving computer-readable information.

The system and various devices also typically will include a number of software applications, modules, services or other elements located within at least one working memory device, including an operating system and application programs such as a client application or Web browser. It should be appreciated that alternate embodiments may have numerous variations from that described above. For example, customized hardware might also be used and/or particular elements might be implemented in hardware, software (including portable software, such as applets) or both. Further, connection to other computing devices such as network input/output devices may be employed. Storage media and other non-transitory computer readable media for containing code, or portions of code, can include any appropriate media known or used in the art, such as but not limited to volatile and non-volatile, removable and non-removable media implemented in any method or technology for storage of information such as computer readable instructions, data structures, program modules or other data, including RAM, ROM, EEPROM, flash memory or other memory technology, CD-ROM, digital versatile disk (DVD) or other optical storage, magnetic cassettes, magnetic tape, magnetic disk storage or other magnetic storage devices or any other medium which can be used to store the desired information and which can be accessed by a system device. Based on the disclosure and teachings provided herein, a person of ordinary skill in the art will appreciate other ways and/or methods to implement the various embodiments.

The specification and drawings are, accordingly, to be regarded in an illustrative rather than a restrictive sense. It will, however, be evident that various modifications and changes may be made thereunto without departing from the broader spirit and scope of the invention as set forth in the claims.

What is claimed is:

1. A computer-implemented method, comprising:
receiving an input image;
receiving a request for at least one insight related to the input image;
analyzing the input image to detect one or more anomalies present in the input image;
utilizing at least one neural network to infer information associated with the input image;
generating a plurality of reports related to the input image based, at least in part, upon the inferred information, wherein each of the plurality of reports have at least one associated metric associated with the inferred information in the respective report; and
presenting the plurality of reports as a histogram based, at least in part, on the associated metric for the respective inferred information, wherein the histogram includes one or more peaks associated with a frequency distribution across a range, and the one or more peaks correspond to different inferred information.

2. The computer-implemented method of claim 1, wherein the at least one neural network is trained using at least one of an image model, a text model, and historical data.

3. The computer-implemented method of claim 1, further comprising:
enabling a user to interact with at least a portion of one of a report in the plurality of reports and the input image; and
providing an indication on an other of the report and the input image corresponding to the interacted portion of the report.

4. The computer-implemented method of claim 1, further comprising:
enabling a user to interact with the plurality of reports, wherein an interaction includes one or more of: highlighting in the input image or a report of the plurality of reports by a user, receiving a question associated with the plurality of reports from the user, or an interaction with the histogram generated for the plurality of reports.

5. The computer-implemented method of claim 1, wherein
the input image is obtained through a medical imaging process.

6. The computer-implemented method of claim 1, wherein the histogram is configured to provide a comprehensive presentation of the plurality of reports.

7. A computer-implemented method, comprising:
receiving an input image;
generating, using a machine learning model, at least one inference associated with the image;
providing a first output for display based, at least in part, upon the at least one inference, the first output provided as part of a histogram including at least a first peak and a second peak;
receiving at least one interaction with a selected second peak of the first output, the at least one interaction corresponding to a selection of one or more features associated with the at least one inference corresponding to the selected second peak; and
providing at least one second output for display in response to the received at least one interaction, the second output including one or more indications associated with the at least one inference of the selected second peak.

8. The computer-implemented method of claim 7, wherein the first output includes a set of reports associated with the at least one inference.

9. The computer-implemented method of claim 7, wherein the at least one second output includes one or more of: an answer in response to the at least one interaction, and a new set of reports generated in response to the at least one interaction.

10. The computer-implemented method of claim 7, wherein the at least one interaction includes one or more of: highlighting in the first output by a user, receiving a question from the user, or an interaction with the histogram generated for the first output.

11. The computer-implemented method of claim 10, wherein the histogram generated for the first output provides insight as to a clinical diagnosis associated with the input image.

12. The computer-implemented method of claim 7, further comprising:
  enabling a user to interact with at least a portion of a report in the first output; and
  providing an indication on the input image corresponding to the interacted portion of the report.

13. The computer-implemented method of claim 7, wherein the input image is obtained through a medical imaging process.

14. The computer-implemented method of claim 7, wherein the machine learning model is trained using at least one of an image model, a text model, and historical data.

15. The computer-implemented method of claim 7, wherein the histogram is configured to provide a comprehensive presentation of a plurality of reports.

* * * * *